United States Patent [19]
Hähndel et al.

[11] Patent Number: 6,074,365
[45] Date of Patent: Jun. 13, 2000

[54] FERROFLUID-SUPPORTED ELECTROMAGNETIC DRIVE FOR A BLOOD PUMP FOR SUPPORTING THE HEART OR PARTIALLY OR TOTALLY REPLACING THE HEART

[76] Inventors: Thomas Hähndel, Kirchstrasse 20, Roitzsch, Germany, D 06809; Hanns-Dietrich Stahlmann, Obstallee 29, Berlin, Germany, D 13593; Arnim Nethe, Sternstrasse 4, Berlin, Germany, D 13359; Johannes Müller, Güntzelstrasse 63, Berlin, Germany, D 10717; Norbert Buske, Eschenbachstrasse 4, Berlin, Germany, D 12437; Armin Rehfeld, Tempelhofer Damm 56, Berlin, Germany, D 12101

[21] Appl. No.: 08/945,780
[22] PCT Filed: Feb. 27, 1997
[86] PCT No.: PCT/DE97/00441
  § 371 Date: Jan. 26, 1998
  § 102(e) Date: Jan. 26, 1998
[87] PCT Pub. No.: WO97/31662
  PCT Pub. Date: Sep. 4, 1997

[30] Foreign Application Priority Data
  Feb. 27, 1996 [DE] Germany .................. 196 09 281

[51] Int. Cl.[7] .................. A61M 1/00; A61M 1/10
[52] U.S. Cl. .................. 604/151; 623/3
[58] Field of Search .................. 604/151, 152, 604/153; 623/3; 128/899; 600/16, 9, 12; 417/412

[56] References Cited

U.S. PATENT DOCUMENTS

| | | |
|---|---|---|
| 3,768,931 | 10/1973 | Willis, Jr. |
| 3,874,002 | 4/1975 | Kurpanek |
| 4,650,485 | 3/1987 | Della Sala |
| 4,869,656 | 9/1989 | Della Sala .................. 417/412 |

FOREIGN PATENT DOCUMENTS

| | | |
|---|---|---|
| 0272445 | 6/1988 | European Pat. Off. |
| 0454353 | 10/1991 | European Pat. Off. |
| 160532 | 8/1983 | Germany |
| 2079381 | 1/1982 | United Kingdom |

*Primary Examiner*—Mark O. Polutta
*Assistant Examiner*—Michael J. Hayes
*Attorney, Agent, or Firm*—Horst M. Kasper

[57] ABSTRACT

The invention relates to a magnetofluid-supported electromagnetic drive for a blood pump for supporting or partially to totally replacing the heart whereby the blood pump in its weight as well as its energy density nearly corresponds to the natural heart and is especially suitable for an implantation whereby a reduction of the total system in comparison with known systems is to be made possible and the efficiency is improved at the same time. This task is solved by the blood pump having a magnetofluid-supported electromagnetic drive consisting of one or several electromagnets and force-transforming facilities and with the space of at least one electromagnetic circuit being completely or partially filled with magnetofluid, whereby the poles show permanent-magnetic properties. Thereby, a magnetofluid with a saturation magnetization of 150 to 450 mT has been used with an initial permeability of 5 to 25.

11 Claims, 3 Drawing Sheets

FERROFLUID-SUPPORTED ELECTROMAGNETIC DRIVE FOR A BLOOD PUMP FOR SUPPORTING THE HEART OR PARTIALLY OR TOTALLY REPLACING THE HEART

FIELD OF THE INVENTION

This invention relates to a ferrofluid-supported electromagnetic drive for a blood pump for supporting the heart or partially or totally replacing the heart. It consists of one or several electromagnets and force-transforming facilities as it is known from the U.S. Pat. No. 4,650,485.

BACKGROUND OF THE INVENTION

In the last years, external and implantable ventricular assist devices have been increasingly used as a bridging up to the transplantation of a donor heart. The experience gained with these ventricular assist devices have caused new considerations to that extent that these ventricular assist devices should not only be used for bridging up to the transplantation of a donor heart, but also as a long-term measure. Several aspects speak for this. The organs available for a transplantation are rare. The use of an artificial assist devices can stabilise and improve the condition of the patient so that the preconditions for such a transplantation will be more favourable. The main problem of the transplantation of donor organs, namely the repulsion reaction does not occur with artificial supportive systems. An artificial assist device can possibly also result in a recuperation of the damaged heart so that the patient can continue to live with his native heart.

Different supportive systems are tested and used. In general, they only differ in the type of drive.

Electromagnetic systems consist of an electromagnet squeezing out a blood pouch in order to supply the blood. Such an arrangement has been described in detail in the U.S. Pat. No. 3,874,002. Using an electrical motor, electromechanical systems generate a rotation movement which is transformed into a pump movement. Furthermore, electrohydraulic and electropneumatic systems are known in which a liquid or a gas are pumped into a chamber using a hydraulic pump or a compressor in order to move a flexible membrane for the blood supply.

An attempt was made to develop ferrofluid-driven systems as it is known from the above-mentioned U.S. Pat. No. 4,650,485. Using this known blood pump, the membrane of the blood chamber shall directly be moved by a magnetofluid which is excited by a magnetic field to do so. Unfortunately, such an arrangement will not be able to generate the pump pressure required for its purpose of application if the exciter coil systems are not chosen big enough. Therefore this blood pump is not suitable for implantation.

Magnetofluids are stable dispersions with supermagnetic properties. They consist of single domain particles which are available in a homogenous distribution in selectable solvents by means of surface-active substances. The homogenous distribution is also kept in the strong magnetic field (gradient). The DD-Description of the Invention 160 532 describes such a magnetofluid in detail. Magnetofluids with initial permeabilities up to 4 and saturation magnetisations up to 100 mT are known and have been described.

Because of their simple structure and the sturdiness connected with it, mainly electromagnetic drives have gained acceptance.

With regard to the known systems of this kind, there is a high discrepancy between the design and the size on the one hand and the efficiency with the expenditures for energy supply linked with it on the other. Apart from acoustical disturbances, these are factors which demonstrate essential loads for the patient who is stressed anyway.

The invention is based on the task to create a drive for a blood pump for supporting or partially to totally replacing the heart whereby the blood pump in its weight as well as its energy density nearly corresponds to the natural heart and is especially suitable for an implantation whereby a reduction of the total system in comparison with known systems is made possible and the efficiency is improved at the same time.

This task is solved by the blood pump having a ferrofluid-supported electromagnetic drive consisting of one or several electromagnets and force-transforming facilities and with the space of at least one electromagnetic circuit being completely or partially filled with magnetofluid, whereby the poles show permanent-magnetic properties. Thereby, a magnetofluid with a saturation magnetisation of 150 to 450 mT has been used with an initial permeability of 5 to 25, consisting of single domain particles from iron, cobalt or iron/cobalt alloys, a liquid carrier and surface-active substances which effect the colloidal stability of the single domain particles.

The main idea of the invention is that the effect of the space is increased by the applied ferrofluid (ferrofluid, magnet liquid) because of its higher permeability.

This is succeeded because the transition from the highly permeable back-circuit to the fluid results in an increase of the force (Maxwell stress). Moreover, the underpressure of the magnetofluid can be used under certain circumstances. This underpressure is caused that force densities which are directed out from the magnetofluid occur at its free surface (for example to air) under the effect of a magnetic field.

At last, lower excitations are sufficient for the generation of the required pump pressure. This permits a reduction of the drive size and decreases the losses. This improvement is directly linked with the size of the initial permeability and the saturation magnetisation. Due to the magnetofluid, the mechanical impact at the end of the attraction process is also lowered between the poles.

The drive can be directly put on a blood pump in its simplest design as a one-chamber system. In more complicated designs, a two-chamber or four-chamber system is also possible. Thereby, designs in series as well as parallel arrangements are possible as well.

Therefore, the drive can be used in simple coronary circulation supportive systems or can be applied as a partial or even total replacement of the heart in a simulation of the heart function that is as lifelike as possible.

In the following, the invention is described in detail by means of an embodiment which is designed as a one-stage operation shown in the drawing.

DETAILED DESCRIPTION

Figure 1:
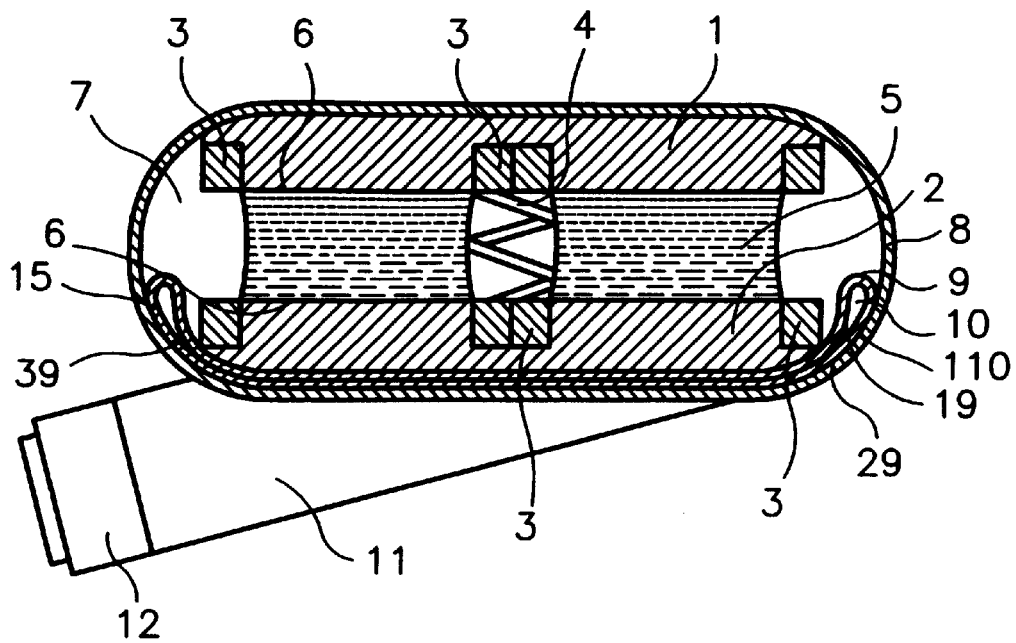
FIG. 1 Cross-section of the artificial heart drive with the chamber compressed.

FIG. 1 shows the principle of the drive schematically for a one-chamber system in a sectional drawing.

The ventricular capacity 10 is tightly enclosed by the ventricular wall 9 of the blood chamber 110. The upper ventricular wall 19 has been formed as a bending-elastic membrane 39 and has flow-in pipe 11 and flow-out pipes 111 as well as ventricle 12. The flexibility of the ventricular wall 9 permits the squeezing of the ventricular capacity 10 by the drive 1 up to 6. The required load transmission is ensured by the direct contact of the upper ventricular wall 9 with the lower core half 2. The fixation of the resting parts takes place by the housing 8 which has been positively connected with the lower ventricular wall 29 on the one hand and with the upper core half 1 on the other.

According to one aspect of the invention, a housing forms a closed container and a single blood chamber having a diaphragm 15 disposed in the container. An inlet connector is furnished at the single blood chamber and an outlet connector is furnished at the single blood chamber.

An electromagnetic drive is disposed in the container and engages the diaphragm wall for filling the blood chamber by suction force through the inlet connector 113 and for emptying the blood chamber by pressure force through the outlet connector 213. The electro-magnetic drive comprises a first core, a first coil attached to the first core, a second core, a second coil attached to the second core, wherein the second core engages the diaphragm and wherein the coils are operated cyclically as to provide a pulsating motion to the diaphragm. A bias spring biases the first core relative to the second core by exerting a force between the first core and to the second core and thereby pressing the first core away from the second core. A magnetic fluid is disposed in the area of the first core and of the second core for interposing between the first core and the second core upon activation of an electromagnetic field in the area of the first core and of the second core and thereby driving the second core toward the first core and thereby engaging the diaphragm for suction filling the single blood chamber.

The space between the ventricular wall 9 and the housing 8 which remains next to the drive 1 to 6 has been filled with a gaseous substance 7. This makes an open and a closed variant possible. In the first variant, there is an adjustable pressure compensation over 14, in the second, a volume change blood chamber 110 effects a pressure change of the gas 7.

Figure 2:
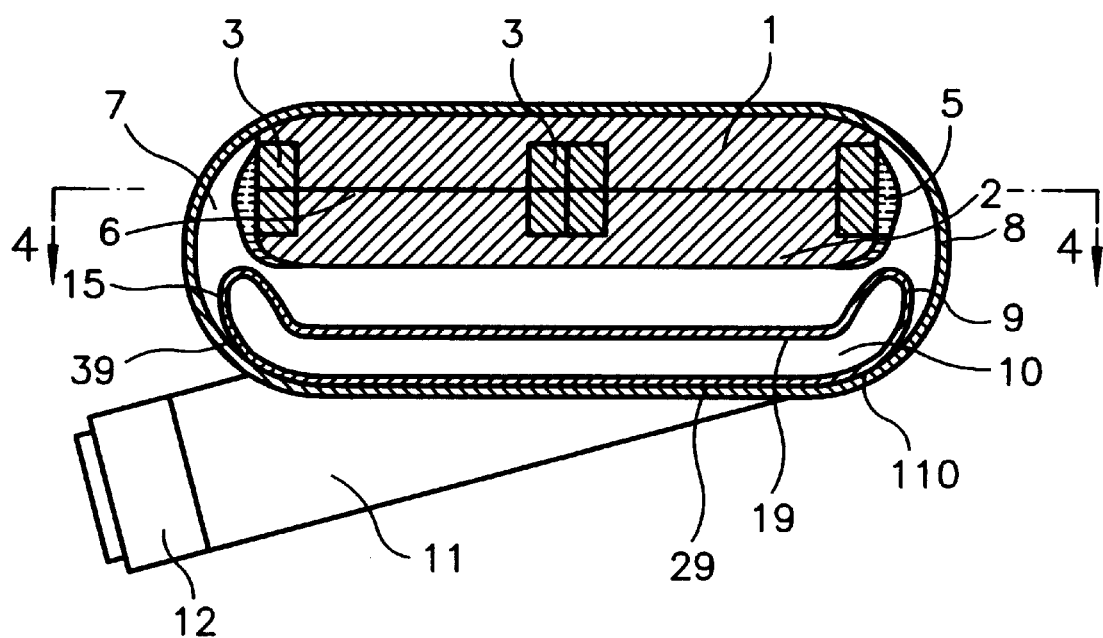
FIG. 2 Cross-section of the artificial heart drive during the suction process.

If the magnetic system formed by the coil pairs 3 and the core halves 1 and 2 is excited, a magnetic field is mainly formed between the poles 6 of the core halves 1 and 2. This will effect that the ferrofluid 5 begins to fill the space between the poles 6 if it is not there anyway due to the existing residual magnetisation. The ferrofluid 5 increases the force action between the poles 6 according to the above-described process. The two core halves 1 and 2 are closed with the ferrofluid 5 escaping from the magnetorheological contraction space. At the same time, the springs 4 are loaded for the driving-out phase. Following this process, an increase of the ventricular capacity 10 and in connection with it a suction process via the opened inlet valve 12 take place due to the elasticity forces of the ventricular wall 9 as shown in FIG. 2.

During the filling phase, the coils are fed via the supply lines from the outside running supplies in duct 14.

Figure 3:
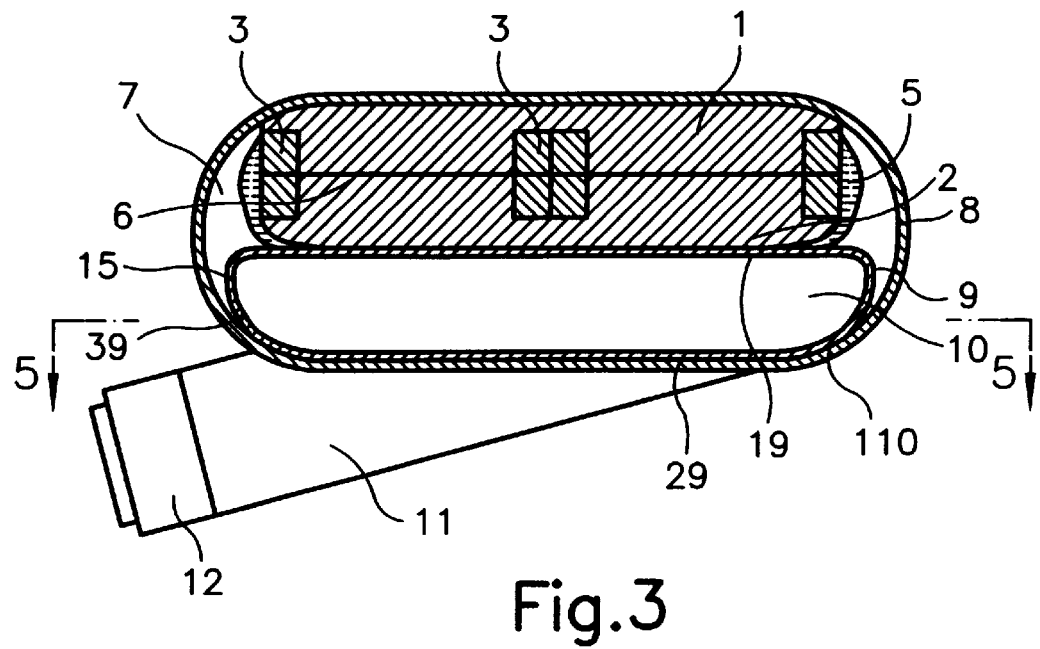
FIG. 3 Cross-section of the artificial heart drive after the suction process has been completed, FIG. 4 Drive in the longitudinal section, FIG. 5 Blood chamber in the sectional drawing.
Figure 4:
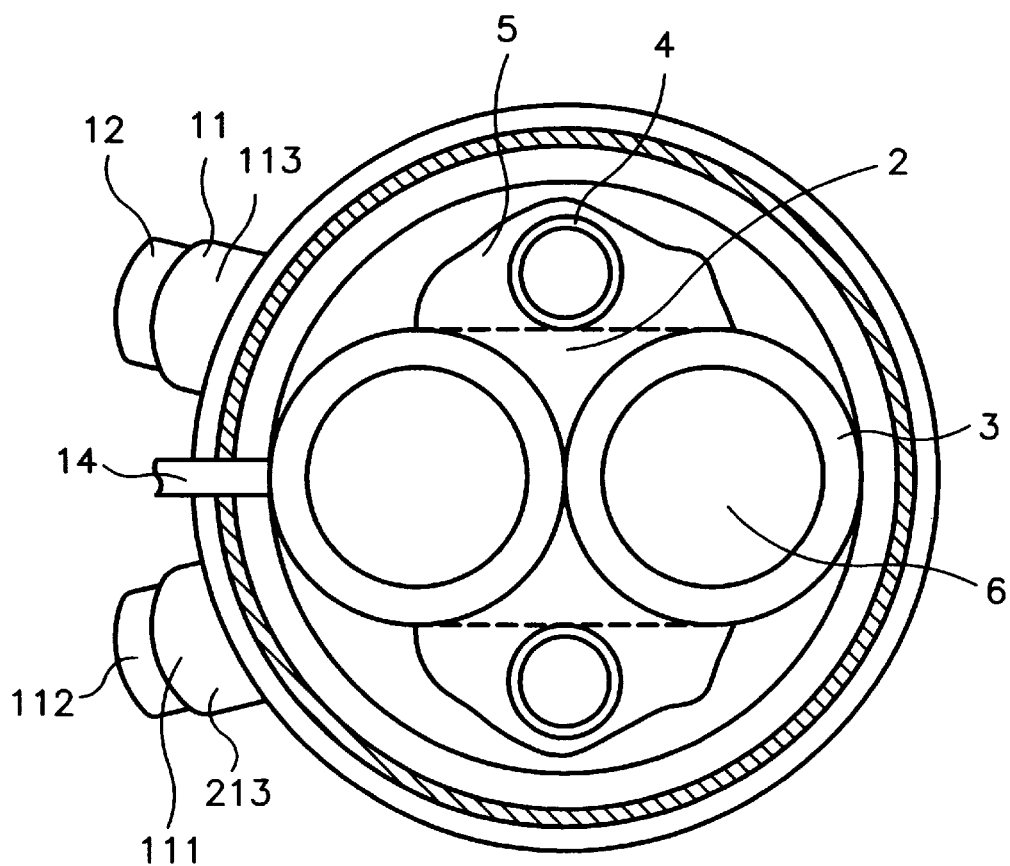
Figure 5:
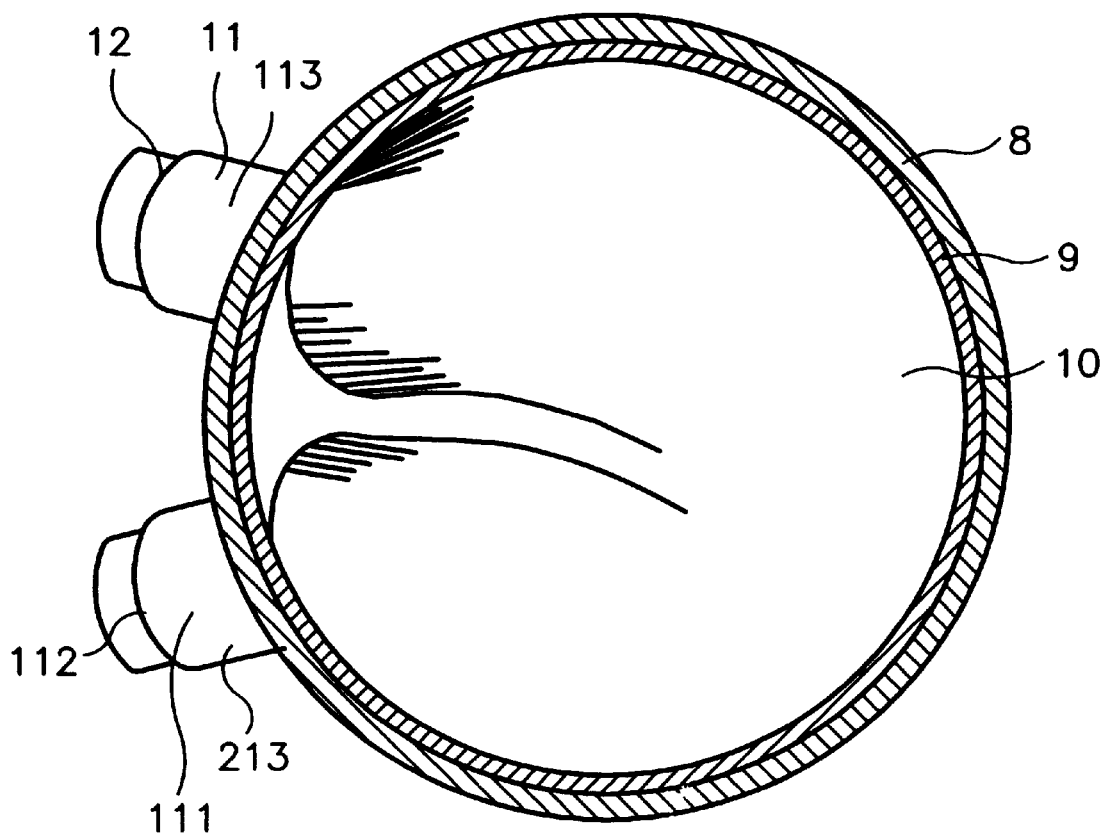

The end of the filling phase is shown in FIG. 3. The excitation is no longer required and the core halves 1 and 2 start to separate due to the loading force of the spring 4. The blood chamber 110 is compressed and the blood is squeezed out through the outlet vale 112.

For the above-described electromagnetic drive of the blood pump, the magnetofluids particularly developed for it with a saturation magnetisation of 120 to 450 mT and initial permeabilities of 5 to 25 are used advantageously. These values which are very high for ferrofluid are reached by using new ferrofluid compositions which contain ferromagnetic single domain particles (iron, cobalt or iron cobalt alloys) in a high concentration which are homogeneously distributed in low-viscous solvents by means of surface-active compounds which are firmly anchored at the particle surface and are well soluble in the respective solvent.

What is claimed is:

1. A ferrofluid-supported electromagnetic drive for a blood pump comprising
   a housing forming a closed chamber;
   a blood chamber creating a ventricular capacity and formed by a lower ventricular wall and an upper ventricular wall with a bending-elastic membrane and having an inlet valve and an outlet valve wherein the blood chamber is disposed in the housing and is attached to the housing by the lower ventricular wall disposed opposite relative to the bending-elastic membrane;
   a magnetic system driving the bending-elastic membrane and provided with an electromagnetic circuit with a space completely or partly filled with ferrofluid.

2. The drive according to claim 1, wherein the electromagnetic circuit is formed by an upper core half, a lower core half and a coil pair enclosing an upper coil surrounding the upper core half and a lower coil surrounding the lower core half wherein the upper core half with the upper coil forms an upper pole and the lower core half with the lower coil forms a lower pole and wherein a magnetic field is formed in the space of the magnetic system created between the upper pole and the lower pole and wherein the upper pole and the lower pole show permanent-magnetic properties.

3. The drive according to claim 2, wherein a spring is inserted between the upper core half and the lower core half forcing the lower core to act on the bending-elastic membrane.

4. The drive according to claim 1, wherein the magnetic system is provided with at least one additional electromagnetic circuit operating with the electromagnetic circuit in series.

5. The drive according to claim 2, wherein a spring is inserted between the upper core half and the lower core half forcing the lower core to act on the bending-elastic membrane.

6. A blood pump essentially consisting of a housing forming a closed container;
   a single blood chamber having a diaphragm wall and disposed in the container;
   an inlet connector furnished at the single blood chamber;
   an outlet connector furnished at the single blood chamber;
   an electro-magnetic drive disposed in the container and engaging the diaphragm wall for filling the blood chamber by suction force through the inlet connector and for emptying the blood chamber by pressure force through the outlet connector;
   wherein the electro-magnetic drive further comprises
      a first core,
      a first coil attached to the first core;
      a second core;

a second coil attached to the second core, wherein the second core engages the diaphragm and wherein the coils are operated cyclically as to provide a pulsating motion to the diaphragm;

a bias spring biasing the first core relative to the second core by exerting a force between the first core and to the second core and thereby pressing the first core away from the second core; and a magnetic fluid disposed in the area of the first core and of the second core for interposing between the first core and the second core upon activation of an electromagnetic field in the area of the first core and of the second core and thereby driving the second core toward the first core and thereby engaging the diaphragm for suction filling the single blood chamber.

7. The blood pump according to claim 6 wherein the electromagnetic drive further comprises an upper core half disposed in the container;

a lower core half disposed in the container;

an upper coil surrounding the upper core half, wherein the upper core half with the upper coil forms an upper pole;

a lower coil surrounding the lower core half, wherein the lower core half with the lower coil forms a lower pole, and wherein a magnetic field is formed in the space of the magnetic system created between the upper pole and the lower pole upon energizing the respective coils and wherein the upper pole and the lower pole show permanent-magnetic properties.

8. A blood pump comprising a blood chamber having a diaphragm wall;

an inlet connector furnished at the blood chamber;

an outlet connector furnished at the blood chamber;

an electro-magnetic drive having a first electromagnetic pole and having a second electro-magnetic pole, wherein the second electro-magnetic pole engages the diaphragm wall;

a bias spring biasing the second pole relative to the first pole by exerting a force between the second pole and the first pole and thereby pressing the first pole away from the second pole for emptying the blood chamber by pressure force through the outlet connector.

9. A method for pumping blood comprising furnishing a blood chamber having a diaphragm wall;

increasing the volume of the blood chamber by expanding the diaphragm wall by removing a second electro-magnetic pole away from the blood chamber based on a magentic attraction exerted by a first electromagnetic pole onto the second electro-magnetic pole;

sucking blood through an inlet connector furnished at the blood chamber into the expanding blood chamber;

decreasing the volume of the blood chamber by contracting the diaphragm wall by pushing the second electro-magnetic pole toward the blood chamber based on a bias spring disposed between the first electro-magnetic pole and the second electro-magnetic pole and exerting a force between the second pole and the first pole and thereby pressing the first pole away from the second pole for emptying the blood chamber by pressure force through the outlet connector;

pressing blood through an outlet connector furnished at the blood chamber out of the contracting blood chamber.

10. The method for pumping blood according to claim 9 further comprising operating the first electro-magnetic pole and the second electro-magnetic pole cyclically for furnishing a pulsating motion to the diaphragm; and interposing a magnetic fluid in the area of the first electro-magnetic pole and of the second electro-magnetic pole upon activation of an electromagnetic field in the area of the first core and of the second core and thereby driving the second electro-magnetic pole toward the first electro-magnetic pole and thereby releasing the diaphragm for suction filling the single blood chamber.

11. The method for pumping blood according to claim 10 further comprising keeping the magnetic fluid outside of the blood chamber.

* * * * *